United States Patent [19]

Collins et al.

[11] 4,328,355
[45] May 4, 1982

[54] PROSTAGLANDIN DERIVATIVES HAVING ARYL, HYDROXYL, AND ALKYNYL FUNCTIONS IN ONE SIDE CHAIN

[75] Inventors: Paul W. Collins, Deerfield; Raphael Pappo, Skokie, both of Ill.

[73] Assignee: G. D. Searle & Co., Skokie, Ill.

[21] Appl. No.: 73,983

[22] Filed: Sep. 10, 1979

Related U.S. Application Data

[63] Continuation-in-part of Ser. No. 754,157, Dec. 27, 1976, abandoned.

[51] Int. Cl.$^3$ ............................................. C07C 177/00
[52] U.S. Cl. ........................................ 560/53; 562/463
[58] Field of Search ............................ 560/53; 562/463

[56] References Cited

U.S. PATENT DOCUMENTS

| | | | |
|---|---|---|---|
| 3,894,062 | 7/1975 | Morozowich et al. | 560/66 |
| 3,978,114 | 8/1976 | Yankee | 560/53 |
| 4,104,474 | 8/1978 | Smith | 560/53 |
| 4,198,430 | 4/1980 | Gandolfi | 560/53 |

FOREIGN PATENT DOCUMENTS 2154309  5/1972  Fed. Rep. of Germany ........ 560/53

OTHER PUBLICATIONS

Derwent Abstract 47726A/27, BE 862363, 27-06-78.

*Primary Examiner*—Paul J. Killos
*Attorney, Agent, or Firm*—Albert Tockman; Mary Jo Kanady; James G. Passe

[57] ABSTRACT

A compound of the formula

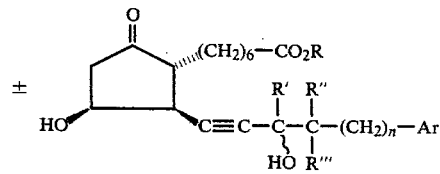

wherein R is hydrogen or lower alkyl having 1–7 carbon atoms; R', R", and R''' are each individually hydrogen or methyl; n is 0–3; and Ar is phenyl, halosubstituted phenyl, lower alkyl substituted phenyl wherein the lower alkyl contains 1–4 carbon atoms, lower alkoxy substituted phenyl wherein the lower alkoxy contains 1–4 carbon atoms, p-biphenyl, or trifluoromethyl substituted phenyl. Compounds of the present invention are useful as antifertility agents.

20 Claims, No Drawings

PROSTAGLANDIN DERIVATIVES HAVING ARYL, HYDROXYL, AND ALKYNYL FUNCTIONS IN ONE SIDE CHAIN

This is a continuation-in-part of application Ser. No. 754,157 filed Dec. 27, 1976, now abandoned.

The present invention encompasses a compound of the formula

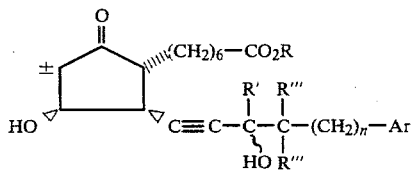

wherein R is hydrogen or lower alkyl having 1-7 carbon atoms; R', R" and R''' are each individually hydrogen or methyl; n is 0-3; and Ar is phenyl, halosubstituted phenyl, lower alkyl substituted phenyl wherein the lower alkyl contains 1-4 carbon atoms, lower alkoxy substituted phenyl wherein the lower alkoxy contains 1-4 carbon atoms, p-biphenyl, or trifluoromethyl substituted phenyl, and the wavy line represents R or S stereochemistry.

Lower alkyl having 1-7 carbon atoms refers to methyl, ethyl, propyl, butyl, pentyl, hexyl, heptyl radicals and branched chain isomers thereof.

Lower alkyl substituted phenyl refers to tolyl, phenethyl, p-tertiary butyl phenyl, p-propyl phenyl and the like.

Halo substituted phenyl refers to chlorophenyl, fluorophenyl, bromophenyl, and iodophenyl.

Alkoxy substituted phenyl refers to methoxylphenyl, ethoxylphenyl, propoxyphenyl, and butoxyphenyl.

In general —CR"R'''—(CH$_2$)$_n$— is a straight or branched chain alkylene having 1-6 carbon atoms and Ar refers to commonly substituted phenyls.

Crystalline esters of acids of the present invention of the type described in U.S. Pat. No. 3,894,062 are considered equivalent for purposes of the present invention.

Compounds of the formula

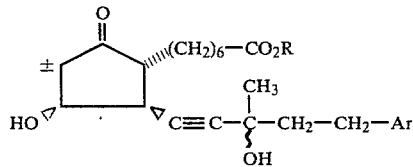

wherein R and Ar are as previously defined are preferred.

Compounds of the present invention are prepared according to the following reaction scheme:

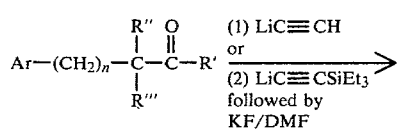

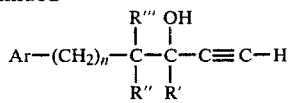

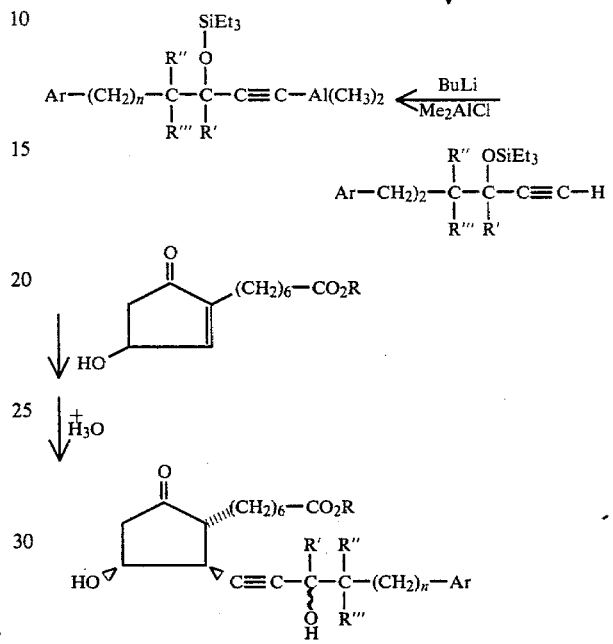

wherein R, R', R", R''', n, and Ar are as previously defined.

Starting materials for preparation of compounds are exemplified by ketones and aldehydes of the formula:

$$R'-\overset{O}{\overset{\|}{C}}-\overset{R''}{\underset{R'''}{\overset{|}{C}}}-(CH_2)_n-Ar$$

| Ar | n | R" | R''' | R' |
|---|---|---|---|---|
| phenyl | 1 | H | H | CH$_3$ |
| m-chlorophenyl | 1 | H | H | CH$_3$ |
| p-fluorophenyl | 1 | H | H | CH$_3$ |
| m-trifluoromethylphenyl | 1 | H | H | CH$_3$ |
| phenyl | 1 | CH$_3$ | CH$_3$ | H |
| phenyl | 2 | H | H | CH$_3$ |
| phenyl | 0 | CH$_3$ | CH$_3$ | H |
| phenyl | 3 | H | H | CH$_3$ |
| phenyl | 2 | H | CH$_3$ | CH$_3$ |
| p-methoxyphenyl | 1 | H | H | CH$_3$ |
| p-methylphenyl | 1 | H | H | CH$_3$ |
| p-ethylphenyl | 1 | H | H | CH$_3$ |
| biphenyl | 1 | H | H | CH$_3$ |

Carboxylic acids are converted to the above ketones and aldehydes by art recognized techniques.

Methyl 7-(3-hydroxy-5-oxocyclopent-1-en-1-yl)heptanoate and the corresponding acid are known starting materials. Example 1 illustrates a preferred method of preparing compounds of the present invention.

The closest prior art appears to be U.S. Pat. No. 3,973,440 which describes PGE$_2$ analogs of the formula:

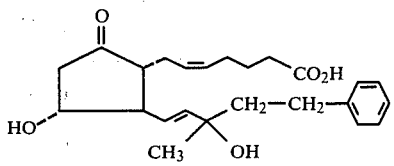

These compounds differ from compounds of the present invention in the stereochemistry at C-11 and in having a —CH=CH at $C_{13}-C_{14}$ instead of —C≡C—. 11-Desoxy compounds of the present invention are disclosed in Belgian Pat. No. 839,533 and U.S. Pat. No. 3,978,114 also discloses related compounds.

Tetrahedron Let. 26, page 2627 (1972) describes compounds of the formula:

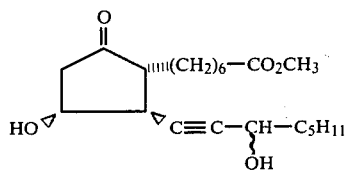

Compounds of the present invention are particularly distinct in that there is a phenyl substituted alkyl radical in place of —$C_5H_{11}$—.

The antifertility activity of the present compounds is illustrated by the following test:

Sexually mature Syrian Golden hamsters 9–10 weeks old are caged with males in the late afternoon. Vaginal smears are taken daily between 8:15 and 10:00 a.m. by means of a pipette. The presence of sperm is considered positive evidence of insemination. The day of insemination is designated as day 1 of pregnancy. Pregnant females are injected daily with test compound beginning on day 1 through day 5. Route of administration is either subcutaneous or intragastric. The daily injection is usually in a volume of 0.2 cc corn oil, however, the volume and vehicle may vary depending on the physical characteristics of the particular compound being tested. All animals are sacrificed with dry ice ($CO_2$) on day 6 in the morning.

The entire reproductive tract is removed and the uterus and ovaries trimmed of extraneous tissue. The total number of implantation sites is counted and recorded. By observation, day 6 size sites are designated as normal and any sites which are smaller and/or pale or resorbing are designated as abnormal.

The total number of corpora lutea are counted and recorded. Again, by observation, the red corpora are considered normal and the pale, pink or white regressed corpora are considered abnormal.

A single dose of compound is classified as active or inactive on the basis of the percent implantation, which is derived by dividing the total number of implantation sites by the total number of corpora lutea and multiplying by 100.

50% Or less implantation rate is considered active
51% Or more implantation rate is considered inactive.

Abnormal implantation sites and corpora lutea are also reported when 20% or more sites are abnormal or if no abnormal sites, only 50% or more abnormal corpora lutea. The $ED_{50}$ of a compound is approximated from inspection or calculated according to the method of Berkson (J. Amer. Stat. Assoc. 48 (263): 565, 1953). Estrone is employed as the standard. A relative potency is obtained from the ratio of the $ED_{50}$ of Estrone to that of the test compound.

Compounds of the present invention may be combined with common pharmaceutical carriers. These compositions can be administered either orally or parenterally. For oral administration tablets, lozenges, capsules, dragees, pills or powders are suitable, while aqueous solutions, non-aqueous solutions or suspensions are appropriate for parenteral administration. Acceptable pharmaceutical carriers are exemplified by gelatin capsules, sugars such as lactose or sucrose, starches such as corn starch or potato starch, cellulose derivatives such as sodium carboxymethyl cellulose, ethyl cellulose, methyl cellulose or cellulose acetate phthalate, gelatin, talc, calcium phosphate such as dicalcium phosphate or tricalcium phosphate, sodium sulfate, calcium sulfate, polyvinylpyrrolidone, acacia, polyvinyl alcohol, stearic acid, alkaline earth metal stearates such as magnesium stearate, vegetable oils such as peanut oil, cottonseed oil, sesame oil, olive oil, corn oil or theobroma, water, agar, alginic acid, benzyl alcohol, isotonic saline and phosphate buffer solutions as well as other non-toxic compatible substances.

The invention will appear more fully from the examples which follow. They are not to be construed as limiting the invention either in spirit or in scope as variations both in materials and in methods will be apparent to those skilled in the art. In the following examples, temperatures are given in degrees centigrade (°C.) and quantity of materials in parts by weight unless parts by volume is specified.

EXAMPLE 1

8 Parts by volume of 2.5 molar n-butyl lithium is added to a solution of 3.1 parts of triethylsilyl acetylene in 20 parts by volume of ethyl ether at −30° C. The resulting solution is allowed to warm to room temperature, then it is cooled again to −30° C. and 3 parts of benzyl acetone is added. The reaction mixture is allowed to warm to room temperature and is then stirred for 1 hour. The reaction mixture is poured into ether and dilute hydrochloric acid. The ethereal layer is washed with water and dried over anhydrous sodium sulfate. The ether is removed under reduced pressure and the residual oil is dissolved in 15 parts by volume of dimethylformamide containing 2 parts of powdered potassium fluoride. This reaction mixture is stirred and heated at 70°–80° C. for 1 hour, after which time it is diluted with water and extracted with ether. The ether layer is separated and washed with water and dried over anhydrous sodium sulfate. The ether is removed under reduced pressure and the residue is chromatographed on silica gel using 30% ethyl acetate/hexane as eluent to provide 3-methyl-3-hydroxy-5-phenyl-1-pentyne.

The hydroxyl group is protected by treating 3.6 parts of 3-methyl-3-hydroxy-5-phenyl-1-pentyne in 15 parts by volume of dimethylformamide successively with 3.5 parts of imidazole and 4.0 parts of triethylsilyl chloride and stirring this mixture for 1 hour at room temperature. The reaction mixture is poured into ether/water and the ethereal layer is washed with water three times, dried over anhydrous sodium sulfate, and then the ether is removed at reduced pressure. Distillation of the residual oil provides 3-methyl-5-phenyl-3-triethylsilyloxy-1-pentyne.

To 1.74 parts of this ether in 10 parts by volume of ethyl ether at −40° C. is added 2.8 parts by volume of 2.17 molar butyl lithium. The resulting reaction mixture is allowed to stand at room temperature for 30 minutes and then is cooled again to −40° C. A solution of 3.7 parts of a 15% by weight solution of dimethylaluminum chloride in hexane is added, and the reaction mixture is allowed to come to room temperature. The resulting reaction mixture is then treated with 1 part of methyl 7-(3-hydroxy-5-oxocyclopent-1-en-1-yl)heptanoate in 10 parts by volume of ethyl ether. The reaction mixture is stirred at room temperature for 1–2 hours and poured into ether and 1 N hydrochloric acid. The ethereal layer is separated, washed with water, and dried over anhydrous sodium sulfate. The ether is removed at reduced pressure. Purification of the residual oil by low pressure liquid chromatography on silica gel using 30% ethyl acetate/hexane as eluent provides an intermediate of the formula:

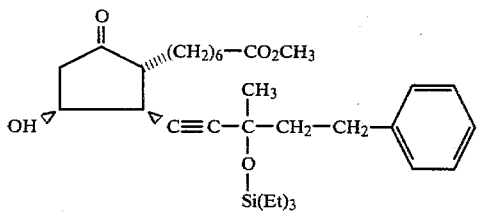

This material is hydrolyzed overnight at room temperature using a 3:1:1 acetic acid:water:tetrahydrofuran mixture. The reaction mixture is diluted with ether and washed 6 times with water and dried over anhydrous sodium sulfate and the solvent is removed. Low pressure liquid chromatography on silica gel using 100% ethyl acetate as eluent provides racemic methyl 7-[3β-hydroxy-2β-(3(R)-hydroxy-3-methyl-5-phenyl-1-pentyn-1-yl)-5-oxocyclopent-1α-yl]heptanoate having the structural formula:

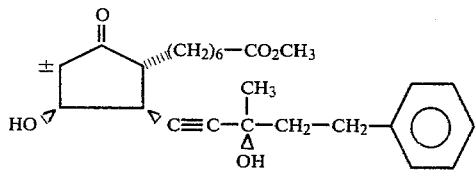

and racemic methyl 7-[3β-hydroxy-2β(3(S)-hydroxy-3-methyl-5-phenyl-1-pentyn-1-yl)-5-oxocyclopent-1α-yl]heptanoate having the structural formula:

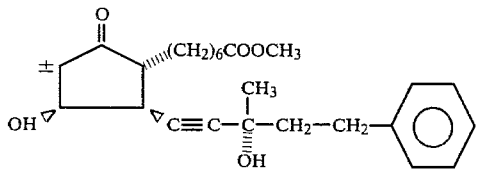

Compound 1 is characterized by nuclear magnetic resonance spectrum peaks at δ1.56, δ3.66 and δ7.21. Compound 1 is active in the hereinbefore described antifertility test at 50–200 μg per hamster.

EXAMPLE 2 m-Trifluoromethyl cinnamic acid is hydrogenated at room temperature at 2 psi using palladium on carbon as catalyst to provide m-trifluoromethylbenzyl acetic acid. 21.8 Parts of this acid is dissolved in 200 parts by volume of ether. Then 100 parts by volume of 1.0 molar methyl lithium in ether is added dropwise over a 30-minute period at 0°. After the addition is complete the mixture is allowed to stir at room temperature for 3–4 hours. The mixture is poured into 1 N HCl, the organic layer is washed successively with water and 5% potassium carbonate, and then dried over anhydrous sodium sulfate. The solvent is removed to provide m-trifluoromethylbenzyl acetone. Following the procedure set out in Example 1, replacing benzyl acetone with m-trifluoromethyl benzylacetone provides racemic methyl 7-[3β-hydroxy-2β-(3(R)-hydroxy-3-methyl-5-m-trifluoromethylphenyl-1-pentyn-1-yl)-5-oxocyclopent-1α-yl]heptanoate:

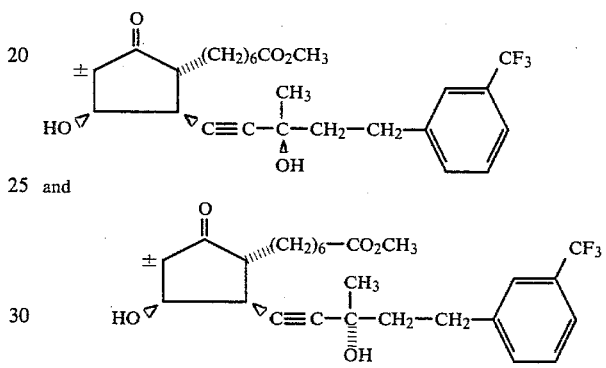

racemic methyl 7-[3β-hydroxy-2β-(3(S)-hydroxy-3-methyl-5-m-trifluoromethylphenyl-1-pentyn-1-yl)-5-oxocyclopent-1α-yl]heptanoate.

In a similar manner p-fluorocinnamic acid is converted to racemic methyl 7-[3β-hydroxy-2β-(3(S)-hydroxy-3-methyl-5p-fluorophenyl-1-pentyn-1-yl)-5-oxocyclopent-1α-yl]heptanoate, and the racemic 3R derivative thereof; p-bromocinnamic acid is converted to racemic methyl 7-[3β-hydroxy-2β-(3(S)-hydroxy-3-methyl-5-p-bromophenyl-1-pentyn-1yl)-5-oxocyclopent-1α-yl]heptanoate, and the racemic 3R derivative thereof; m-chlorocinnamic acid is converted to racemic methyl 7-[3β-hydroxy-2β(3(S)-hydroxy-3-methyl-5-m-chlorophenyl-1-pentyl-1yl)-5-oxocyclopent-1α-yl]heptanoate, and the racemic 3R derivative thereof; p-methylcinnamic acid is converted to racemic methyl 7-[3β-hydroxy-2β-(3(S)-hydroxy-3-methyl-5-p-methylphenyl-1-pentyn-1yl)-5-oxocyclopent-1α-yl]heptanoate, and the racemic 3R derivative thereof; p-ethylcinnamic acid is converted to racemic methyl 7-[3β-hydroxy-2β-(3(S)-hydroxy-3-methyl-5-p-ethylphenyl-1-pentyn-1-yl)-5-oxocyclopent-1α-ly]heptanoate, and the racemic 3R derivative thereof; p-methoxycinnamic acid is converted to racemic methyl 7-[3β-hydroxy-2β-(3(S)-hydroxy-3-methyl-5-p-methoxyphenyl-1-pentyn-1yl)-5-oxocyclopent-1α-yl]heptanoate, and the racemic 3R derivative thereof; and p-phenylcinnamic acid is converted to racemic methyl 7-[3β-hydroxy-2β-(3(S)-hydroxy-3-methyl-5-p-biphenyl-1-pentyn-1-yl)-5-oxocyclopent-1α-yl]heptanoate, and the racemic 3R derivative thereof.

4-Phenylbutyric acid is converted to racemic methyl 7[3β-hydroxy-2β-(3(S)-hydroxy-3-methyl-6-phenyl-1-hexyn-1-yl-5-oxocyclopent-1α-yl]heptanoate and the 3R derivative thereof.

EXAMPLE 3

Replacing benzyl acetone with benzyldimethyl acetaldehyde and following the procedure in Example 1 provides racemic methyl 7-[3β-hydroxy-2β-(3(R)-hydroxy-4,4,dimethyl-5phenyl-1-pentyn-1-yl)-5-oxocyclopent-1α-yl]heptanoate having the following structural formula:

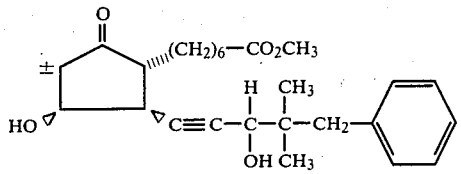

and racemic methyl 7-[3β-hydroxy-2β-(3(S)-hydroxy-4,4,dimethyl-5-phenyl-1-pentyl-1yl)-5-oxocyclopent-1α-yl]heptanoate having the following structural formula:

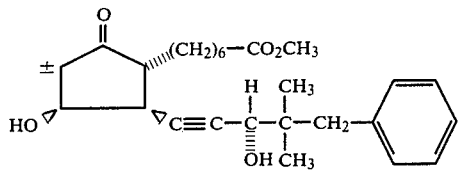

EXAMPLE 4

Following the procedures in Examples 1 and 2 and using m-chlorophenylacetone and 7-(3-hydroxy-5-oxocyclopent-1-en-1-yl)heptanoate provides racemic methyl 7-[3β-hydroxy-2β-(3(S)-hydroxy-3-methyl-4m-chlorophenyl-1butyn-1-yl)-5-oxocyclopent-1α-yl]heptanoate and the (3R) stereoisomer thereof having the following structural formula:

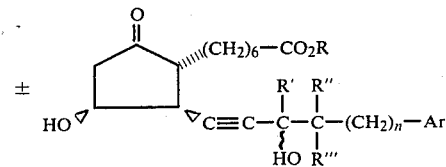

What is claimed is:
1. A compound of the formula

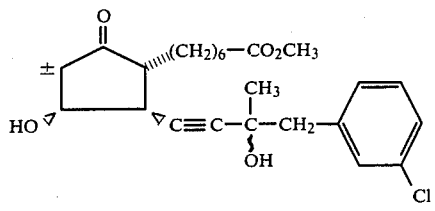

wherein R is hydrogen or lower alkyl having 1–7 carbon atoms; R', R", and R''' are each individually hydrogen or methyl; n is 0–3; and Ar is phenyl, halosubstituted phenyl, lower alkyl substituted phenyl wherein the lower alkyl contains 1–4 carbon atoms, lower alkoxy substituted phenyl wherein the lower alkoxy contains 1–4 carbon atoms, p-biphenyl, or trifluoromethyl substituted phenyl, and the wavy line represents R or S stereochemistry.

2. A compound according to claim 1 of the formula:

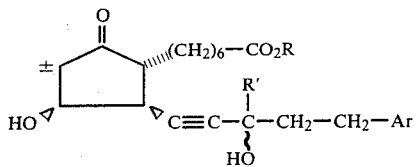

wherein R is hydrogen or lower alkyl having 1–7 carbon atoms; R' is hydrogen or methyl; and Ar is phenyl, halosubstituted phenyl, lower alkyl substituted phenyl wherein the lower alkyl contains 1–4 carbon atoms, lower alkoxy substituted phenyl wherein the lower alkoxy contains 1–4 carbon atoms, p-biphenyl, or trifluoromethyl substituted phenyl, and the wavy line represents R or S stereochemistry.

3. A compound according to claim 1 which is racemic methyl 7-[3β-hydroxy-2β-(3(S)-hydroxy-3-methyl-5-phenyl-1-pentyn-1-yl)-5-oxocyclopent-1α-yl]heptanoate.

4. A compound according to claim 1 which is racemic methyl-7-[3β-hydroxy-2β-(3(R)-hydroxy-3-methyl-5-phenyl-1-pentyn-1-yl)-5-oxocyclopent-1α-yl]heptanoate.

5. A compound according to claim 1 which is racemic methyl 7-[3β-hydroxy-2β-(3(R)-hydroxy-3-methyl-5-m-trifluoromethylphenyl-1-pentyn-1-yl)-5-oxocyclopent-1α-yl]heptanoate.

6. A compound according to claim 1 which is racemic methyl 7-[3β-hydroxy-2β-(3(S)-hydroxy-3-methyl-5-m-trifluoromethylphenyl-1-pentyn-1-yl)-5-oxocyclopent-1α-yl]heptanoate.

7. A compound according to claim 1 which is racemic methyl 7-[3β-hydroxy-2β-(3(S)-hydroxy-3-methyl-5-m-chlorophenyl-1-pentyn-1-yl)-5-oxocyclopent-1α-yl]heptanoate.

8. A compound according to claim 1 which is racemic methyl 7-[3β-hydroxy-2β-(3(R)-hydroxy-3-methyl-5-m-chlorophenyl-1-pentyn-1-yl)-5-oxocyclopent-1α-yl]heptanoate.

9. A compound according to claim 1 which is racemic methyl 7-[3β-hydroxy-2β-(3(S)-hydroxy-3-methyl-5-p-methylphenyl-1-pentyn-1yl)-5-oxocyclopent-1α-yl]heptanoate.

10. A compound according to claim 1 which is racemic methyl 7-[3β-hydroxy-2β-(3(R)-hydroxy-3-methyl-5-p-methylphenyl-1-pentyn-1-yl)-5-oxocyclopent-1α-yl]heptanoate.

11. A compound according to claim 1 which is racemic methyl 7[3β-hydroxy-2β-(3(S)-hydroxy-3-methyl-5-p-methoxyphenyl-1-pentyn-1-yl)-5-oxocyclopent-1β-yl]heptanoate.

12. A compound according to claim 1 which is racemic methyl 7-[3β-hydroxy-2β-(3(R)-hydroxy-3-methyl-5-p-methoxyphenyl-1-pentyn-1-yl)-5-oxocyclopent-1α-yl]heptanoate.

13. A compound according to claim 1 which is racemic methyl 7-[3β-hydroxy-2β-(3(S)-hydroxy-3-methyl-5-p-biphenyl-1-pentyn-1yl)-5-oxocyclopent-1α-yl]heptanoate.

14. A compound according to claim 1 which is racemic methyl 7-[3β-hydroxy-2β-(3(R)-hydroxy-3-methyl- 5-p-biphenyl-1-pentyn-1-yl)-5-oxocyclopent-1α-yl]heptanoate.

15. A compound according to claim 1 which is racemic methyl-7-[3β-hydroxy-2β-(3(S)-hydroxy-3-methyl-6-phenyl-1-hexyn-1-yl)-5-oxocyclopent-1α-yl]heptanoate.

16. A compound according to claim 1 which is racemic methyl 7-[3β-hydroxy-2β-(3(R)-hydroxy-3-methyl-6-phenyl-1-hexyn-1-yl)-5-oxocyclopent-1α-yl]heptanoate.

17. A compound according to claim 1 which is racemic methyl 7-[3β-hydroxy-2β-(3(R)-hydroxy-4,4-dimethyl-5-phenyl-1-pentyn-1-yl)-5-oxocyclopent-1α-yl]heptanoate.

18. A compound according to claim 1 which is racemic methyl 7-[3β-hydroxy-2β-(3(S)-hydroxy-4,4-dimethyl-5-phenyl-1-pentyn-1-yl)-5-oxocyclopent-1α-yl]heptanoate.

19. A compound according to claim 1 which is racemic methyl 7-[3β-hydroxy-2β-(3(S)-hydroxy-3-methyl-4-m-chlorophenyl-1butyn-1yl)-5-oxocyclopent-1α-yl]heptanoate.

20. A compound according to claim 1 which is racemic methyl 7-[3β-hydroxy-2β-(3(R)-hydroxy-3-methyl-4-m-chlorophenyl-1-butyn-1-yl)-5-oxocyclopent-1α-yl]heptanoate.

* * * * *